(12) United States Patent
Ouali et al.

(10) Patent No.: US 11,291,969 B2
(45) Date of Patent: Apr. 5, 2022

(54) PROCESS FOR PREPARING MICROCAPSULES

(71) Applicant: FIRMENICH SA, Satigny (CH)

(72) Inventors: Lahoussine Ouali, Geneva (CH); Marlène Jacquemond, Geneva (CH)

(73) Assignee: FIRMENICH SA, Geneva (CH)

( * ) Notice: Subject to any disclaimer, the term of this patent is extended or adjusted under 35 U.S.C. 154(b) by 171 days.

(21) Appl. No.: 16/622,106

(22) PCT Filed: Jun. 27, 2018

(86) PCT No.: PCT/EP2018/067273
§ 371 (c)(1),
(2) Date: Dec. 12, 2019

(87) PCT Pub. No.: WO2019/002380
PCT Pub. Date: Jan. 3, 2019

(65) Prior Publication Data
US 2020/0129947 A1    Apr. 30, 2020

(30) Foreign Application Priority Data
Jun. 27, 2017   (EP) ..................................... 17178019

(51) Int. Cl.
| | | |
|---|---|---|
| *B01J 13/16* | (2006.01) | |
| *B01J 13/20* | (2006.01) | |
| *C11D 3/50* | (2006.01) | |
| *C11D 17/00* | (2006.01) | |
| *C11D 17/06* | (2006.01) | |

(52) U.S. Cl.
CPC ............... *B01J 13/16* (2013.01); *C11D 3/505* (2013.01); *C11D 17/0008* (2013.01); *C11D 17/06* (2013.01); *B01J 13/20* (2013.01)

(58) Field of Classification Search
CPC ..... C11D 3/505; C11D 17/0008; C11D 17/06; C11D 3/3707; C11D 3/3715; C11D 3/3738; A61Q 19/10; A61Q 13/00; A61Q 19/00; A61K 2800/10; A61K 2800/805; A61K 8/85; A61K 8/86; A61K 8/87; A61K 8/88; A61K 8/891; A61K 8/11; B01J 13/16; B01J 13/20; B01J 13/22
See application file for complete search history.

(56) References Cited

U.S. PATENT DOCUMENTS

| | | | |
|---|---|---|---|
| 4,783,281 A | * | 11/1988 | Bishop .................... C11D 11/02 510/443 |
| 5,962,003 A | | 10/1999 | Shukla et al. |
| 2010/0113552 A1 | * | 5/2010 | Guyon .................... A01N 43/54 514/406 |
| 2016/0346753 A1 | | 12/2016 | Shukla et al. |

FOREIGN PATENT DOCUMENTS

| | | |
|---|---|---|
| CN | 1032118 A | 4/1989 |
| EP | 0671206 A2 | 9/1995 |
| EP | 2300146 B1 | 3/2017 |
| EP | 2579976 B1 | 8/2017 |
| WO | 2007004166 A1 | 1/2007 |
| WO | 2007096790 A1 | 8/2007 |
| WO | 2015091877 A1 | 6/2015 |
| WO | 2016162381 A1 | 10/2016 |

OTHER PUBLICATIONS

Communication pursuant to Article 94(3) in related European Patent Application No. 18732389.4, dated Feb. 16, 2021, 6 pages.
International Search Report and Written Opinion for International Application No. PCT/EP2018/067273, dated Aug. 29, 2018, 12 pages.
Steffen Arctander "Perfume and Flavor Chemicals" 1969, Montclair, NJ USA; 10 pages.

* cited by examiner

*Primary Examiner* — Irina S Zemel
(74) *Attorney, Agent, or Firm* — Armstrong Teasdale LLP (57) ABSTRACT

Described herein is a process for preparing microcapsules. More particularly, the process is characterized by the fact that it requires limited amounts of water for preparing microcapsules. Microcapsules obtainable by the disclosed process as well as consumer products including those microcapsules are also described.

19 Claims, 2 Drawing Sheets

PROCESS FOR PREPARING MICROCAPSULES

CROSS-REFERENCE TO RELATED APPLICATIONS

This application is a U.S. National Phase Application of PCT/EP2018/067273, filed on Jun. 27, 2018, which claims the benefit of priority to European Application Number 17178019.0, filed Jun. 27, 2017, the entire contents of which are hereby incorporated by reference herein.

TECHNICAL FIELD

The present invention relates to a process for preparing microcapsules. More particularly, the process of the invention is characterized by the fact that it requires limited amounts of water for preparing microcapsules. Microcapsules obtainable by said process as well as consumer products comprising those microcapsules are also objects of the invention.

BACKGROUND OF THE INVENTION

Perfumes are widely used in consumer products such as detergents, softeners, shower gel, shampoo and play a very important role in those products since they often drive the consumer's choice for a given product.

One of the problems faced by the perfumery industry lies in the relatively rapid loss of olfactive benefit provided by odoriferous compounds due to their volatility. In order to tailor the release rates of volatiles, delivery systems such as microcapsules containing a perfume, are needed to protect and later release the core payload when triggered. A key requirement from the industry regarding these systems is to survive suspension in challenging bases without physically dissociating or degrading. This is referred to as performance in terms of stability for the delivery system. For instance, fragranced personal and household cleansers containing high levels of aggressive surfactant detergents are very challenging for the stability of microcapsules during storage.

As described above, the performance in terms of stability represents an important requirement for perfume delivery systems. However, these delivery systems also must exhibit good performance in terms of perfume release, either during the wash/lathering phase (blooming) or on dry substrate (skin, hair, textile or home surface) after the wash.

Among the existing microencapsulation processes, microcapsules obtained via interfacial polymerization are widely used. Typically, during this process, an oil-in-water emulsion or a water-in-oil emulsion is prepared with monomers or polymers soluble in oil phase (such as polyisocyanates) and with polymers soluble in water phase (such as polyamine, polyol). Then, under specific conditions (temperature, pH . . . ) those polymers react together at the oil-water interface to form a polymeric shell. An aqueous core-shell microcapsule slurry is thus obtained.

The nature of the shell therefore depends on the nature of the momomers or polymers present respectively in the oil phase and in the water phase. For example, a polyurea shell is obtained when a polyisocyanate reacts with a polyamine whereas a polyurethane shell is obtained when a polyisocyanate reacts with a polyol.

Processes for producing such microcapsules are widely disclosed in the prior art. Examples of processes for the preparation of polyurea- and polyureathane-based microcapsule slurries are for instance described in WO2007/004166, EP 2300146 or yet EP2579976.

Even if processes for preparing microcapsules are widely-known, there is a need for an alternative process for preparing stable microcapsules that would be suitable for different kind of applications.

The present invention satisfies this and other needs of the industry.

SUMMARY OF THE INVENTION

It has now been found that microcapsules encapsulating a hydrophobic active ingredient such as a perfume oil could be obtained by forming a wall formed from the polymerisation of a monomer present in the oil phase with optionally a reactant in the presence of very limited amounts of water or even no water added during the process.

A first object of the invention is therefore a process for preparing a microcapsule slurry, said process comprising the steps of:
 (i) dissolving a monomer in an oil phase comprising a hydrophobic active ingredient, preferably a perfume;
 (ii) preparing a dispersing phase comprising an emulsifier, wherein the dispersing phase is not miscible with the oil phase;
 (iii) adding the oil phase to the dispersing phase to form a two-phases dispersion;
 (iv) applying conditions sufficient to induce interfacial polymerisation and form microcapsules in form of a slurry;
wherein the monomer is susceptible to react during the interfacial polymerisation to form the microcapsules in form of a slurry;
said process being characterized in that the content of water in the dispersing phase is below or equal to 10% by weight based on the total weight of the dispersing phase.

A second object of the invention is a microcapsule slurry obtainable by the process described above.

A third and fourth objects of the invention are respectively a perfuming composition and consumer products comprising said microcapsule slurry.

Unless otherwise specified, % is meant to designate percentages by weight of a composition.

DETAILED DESCRIPTION OF THE INVENTION

Definitions

A "microcapsule", or the similar, in the present invention is meant to designate a capsule having a core-shell structure and that has a particle size distribution in the micron range (e.g. a mean diameter (d(v, 0.5)) comprised between about 1 and 3000 µm) and comprises an external solid oligomer-based shell or a polymeric shell and an internal phase enclosed by the external shell.

By "monomer", it is meant a molecule that, as unit, reacts or binds chemically to form a polymer or supramolecular polymer. According to an embodiment, the monomer reacts during the interfacial polymerization to form microcapsules in the form of a slurry. Microcapsules may result from the reaction between the monomer and a reactant or may result only from the autopolymerization of the monomer.

By "polyurea-based" wall or shell, it is meant that the polymer comprises urea linkages produced by either an amino-functional crosslinker or hydrolysis of isocyanate groups to produce amino groups capable of further reacting with isocyanate groups during interfacial polymerization.

By "polyurethane-based" wall or shell, it is meant that the polymer comprises urethane linkages produced by reaction of a polyol with the isocyanate groups during interfacial polymerization.

For the sake of clarity, by the expression "dispersion" in the present invention it is meant a system in which particles are dispersed in a continuous phase of a different composition and it specifically includes a suspension or an emulsion.

By "hydrophobic active ingredient", it is meant any active ingredient—single ingredient or a mixture of ingredients—which forms a two-phases dispersion when mixed with water.

Hydrophobic active ingredients are preferably chosen from the group consisting of flavor, flavor ingredients, perfume, perfume ingredients, nutraceuticals, cosmetics, insect control agents, biocide actives and mixtures thereof.

The nature and type of the insect control agents present in the hydrophobic internal phase do not warrant a more detailed description here, which in any case would not be exhaustive, the skilled person being able to select them on the basis of its general knowledge and according to the intended use or application.

Examples of such insect control agents are birch, DEET (N,N-diethyl-m-toluamide), essential oil of the lemon eucalyptus (*Corymbia citriodora*) and its active compound p-menthane-3,8-diol (PMD), icaridin (hydroxyethyl isobutyl piperidine carboxylate), Nepelactone, Citronella oil, Neem oil, Bog Myrtle (*Myrica gale*), Dimethyl carbate, Tricyclodecenyl allyl ether, IR3535 (3-[N-Butyl-N-acetyl]-aminopropionic acid, ethyl ester, Ethylhexanediol, Dimethyl phthalate, Metofluthrin, Indalone, SS220, anthranilate-based insect repellents, and mixtures thereof.

According to a particular embodiment, the hydrophobic-active ingredient comprises a mixture of a perfume with another ingredient selected from the group consisting of nutraceuticals, cosmetics, insect control agents and biocide actives.

According to a particular embodiment, the hydrophobic active ingredient comprises a perfume.

According to a particular embodiment, the hydrophobic active ingredient consists of a perfume.

By "perfume oil" (or also "perfume") what is meant here is an ingredient or composition that is a liquid at about 20° C. According to any one of the above embodiments said perfume oil can be a perfuming ingredient alone or a mixture of ingredients in the form of a perfuming composition. As a "perfuming ingredient" it is meant here a compound, which is used for the primary purpose of conferring or modulating an odor. In other words such an ingredient, to be considered as being a perfuming one, must be recognized by a person skilled in the art as being able to at least impart or modify in a positive or pleasant way the odor of a composition, and not just as having an odor. For the purpose of the present invention, perfume oil also includes combination of perfuming ingredients with substances which together improve, enhance or modify the delivery of the perfuming ingredients, such as perfume precursors, emulsions or dispersions, as well as combinations which impart an additional benefit beyond that of modifying or imparting an odor, such as long-lasting, blooming, malodor counteraction, antimicrobial effect, microbial stability, insect control.

The nature and type of the perfuming ingredients present in the hydrophobic internal phase do not warrant a more detailed description here, which in any case would not be exhaustive, the skilled person being able to select them on the basis of its general knowledge and according to intended use or application and the desired organoleptic effect. In general terms, these perfuming ingredients belong to chemical classes as varied as alcohols, aldehydes, ketones, esters, ethers, acetates, nitriles, terpenoids, nitrogenous or sulphurous heterocyclic compounds and essential oils, and said perfuming co-ingredients can be of natural or synthetic origin. Many of these co-ingredients are in any case listed in reference texts such as the book by S. Arctander, Perfume and Flavor Chemicals, 1969, Montclair, N.J., USA, or its more recent versions, or in other works of a similar nature, as well as in the abundant patent literature in the field of perfumery. It is also understood that said ingredients may also be compounds known to release in a controlled manner various types of perfuming compounds.

The perfuming ingredients may be dissolved in a solvent of current use in the perfume industry. The solvent is preferably not an alcohol. Examples of such solvents are diethyl phthalate, isopropyl myristate, Abalyn® (rosin resins, available from Eastman), benzyl benzoate, ethyl citrate, limonene or other terpenes, or isoparaffins. Preferably, the solvent is very hydrophobic and highly sterically hindered, like for example Abalyn® or benzyl benzoate. Preferably the perfume comprises less than 30% of solvent. More preferably the perfume comprises less than 20% and even more preferably less than 10% of solvent, all these percentages being defined by weight relative to the total weight of the perfume. Most preferably, the perfume is essentially free of solvent.

Process for Preparing a Microcapsule Slurry

A first object of the invention is a process for preparing a microcapsule slurry, said process comprising the steps of:
(i) dissolving a monomer in an oil phase comprising a hydrophobic active ingredient, preferably a perfume;
(ii) preparing a dispersing phase comprising an emulsifier, wherein the dispersing phase is not miscible with the oil phase;
(iii) adding the oil phase to the dispersing phase to form a two-phases dispersion;
(iv) applying conditions sufficient to induce interfacial polymerisation and form microcapsules in form of a slurry;

wherein the monomer is susceptible to react during the interfacial polymerisation to form the microcapsules in form of a slurry;

said process being characterized in that the content of water in the dispersing phase is below or equal to 10% by weight based on the total weight of the dispersing phase.

Without being bound by any theory, the Applicant is of the opinion that the dispersing phase having a limited amount of water allows a better control of the reactions kinetic during the interfacial polymerisation resulting in high quality membrane formation.

Furthermore, due to its limited amount of water, even no amount of water, the microcapsule slurry obtained/obtainable by the process of the invention can be used not only in aqueous consumer product (since the dispersing phase is highly miscible with water) but also in anhydrous consumer product (without any drying step).

Thus, the microcapsules obtained by the process of the present invention do not need to be dried when incorporated in anhydrous consumer product leading to a cost-effective process.

Oil Phase

The shell prepared by the process of the invention depends notably on the nature of the monomer added in the oil phase in step (i).

According to a preferred embodiment of the invention, there is used an amount of between 5 and 60%, more preferably between 10 and 50% of oil in the process of the invention, these percentages being defined by weight relative to the total weight of the obtained microcapsule slurry.

According to an embodiment, the monomer added in step (i) is chosen in the group consisting of at least one polyisocyanate having at least two isocyanate functional groups; poly maleic anhydride such as Biphenyltetracarboxylic dianydride; poly acyl chloride such as Terepthaloyl chloride or 1,3,5-Benzenetricarbonyl trichloride; polyepoxide such as poly[(o-cresyl glycidyl ether)-co-formaldehyde]; acrylate monomers such as trimethylolpropane triacrylate and polyalkoxysilane.

The monomer used in the process according to the invention is present in amounts representing from 0.1 to 15%, preferably from 0.5 to 8% and more preferably from 0.5 to 6% by weight of the microcapsule slurry.

According to a particular embodiment, the monomer added in step (i) is at least one polyisocyanate having at least two isocyanate functional groups.

Suitable polyisocyanates used according to the invention include aromatic polyisocyanate, aliphatic polyisocyanate and mixtures thereof. Said polyisocyanate comprises at least 2, preferably at least 3 but may comprise up to 6, or even only 4, isocyanate functional groups. According to a particular embodiment, a triisocyanate (3 isocyanate functional group) is used.

According to one embodiment, said polyisocyanate is an aromatic polyisocyanate.

The term "aromatic polyisocyanate" is meant here as encompassing any polyisocyanate comprising an aromatic moiety. Preferably, it comprises a phenyl, a toluyl, a xylyl, a naphthyl or a diphenyl moiety, more preferably a toluyl or a xylyl moiety. Preferred aromatic polyisocyanates are biurets, polyisocyanurates and trimethylol propane adducts of diisocyanates, more preferably comprising one of the above-cited specific aromatic moieties. More preferably, the aromatic polyisocyanate is a polyisocyanurate of toluene diisocyanate (commercially available from Bayer under the tradename Desmodur® RC), a trimethylol propane-adduct of toluene diisocyanate (commercially available from Bayer under the tradename Desmodur® L75), a trimethylol propane-adduct of xylylene diisocyanate (commercially available from Mitsui Chemicals under the tradename Takenate® D-110N). In a most preferred embodiment, the aromatic polyisocyanate is a trimethylol propane-adduct of xylylene diisocyanate.

According to another embodiment, said polyisocyanate is an aliphatic polyisocyanate.

The term "aliphatic polyisocyanate" is defined as a polyisocyanate which does not comprise any aromatic moiety. Preferred aliphatic polyisocyanates are a trimer of hexamethylene diisocyanate, a trimer of isophorone diisocyanate, a trimethylol propane-adduct of hexamethylene diisocyanate (available from Mitsui Chemicals) or a biuret of hexamethylene diisocyanate (commercially available from Bayer under the tradename Desmodur® N 100), among which a biuret of hexamethylene diisocyanate is even more preferred.

According to another embodiment, the at least one polyisocyanate is in the form of a mixture of at least one aliphatic polyisocyanate and of at least one aromatic polyisocyanate, both comprising at least two or three isocyanate functional groups, such as a mixture of a biuret of hexamethylene diisocyanate with a trimethylol propane-adduct of xylylene diisocyanate, a mixture of a biuret of hexamethylene diisocyanate with a polyisocyanurate of toluene diisocyanate and a mixture of a biuret of hexamethylene diisocyanate with a trimethylol propane-adduct of toluene diisocyanate. Most preferably, it is a mixture of a biuret of hexamethylene diisocyanate with a trimethylol propane-adduct of xylylene diisocyanate. Preferably, when used as a mixture the molar ratio between the aliphatic polyisocyanate and the aromatic polyisocyanate is ranging from 80:20 to 10:90.

Dispersing Phase

According to the invention, the content of water is below or equal to 10%, preferably below or equal to 5%, more preferably below or equal to 3% by weight based on the total weight of the dispersing phase.

According to a particular embodiment, the dispersing phase is free of water.

It should be understood that the process of the invention does not comprise a further step of adding water. In other words, water (if necessary) is added only during step (ii), namely in the dispersing phase.

According to an embodiment, the dispersing phase is hydrophilic.

It has been found that core-shell microcapsules could be obtained by substituting water used in known process from the prior art with solvent(s) preferably chosen in the group consisting of glycerol, 1,4-butanediol, ethylene glycol and mixtures thereof.

The solvent used in the dispersing phase is present in amounts representing from 40 to 95%, preferably from 50 to 90% and more preferably from 50 to 80% by weight of the microcapsule slurry.

According to the invention, the process of the present invention includes the use of an emulsifier that can be non-ionic and/or ionic in the preparation of the dispersant phase. Suitable ionic emulsifiers include in particular gum Arabic, lignin sulfonate, soy protein, sodium caseinate, gelatin, bovine serum albumin, sugar beet pectin, hydrolyzed soy protein, hydrolyzed sericin, Pseudocollagen, Biopolymer SA-N, Pentacare-NA PF, co-polymers of acrylamide and acrylic acid, acrylic co-polymers bearing a sulfonate group, anionic polyvinyl alcohol, cationic polyvinyl alcohol, and mixtures thereof.

Suitable non-ionic emulsifiers are chosen in the group consisting of polyvinylpyrrolidone, polyvinyl alcohol, co-polymers of vinyl ethers and maleic anhydride, modified polyvinyl alcohol, modified starch, modified cellulose, polysaccharides and mixtures thereof.

By "modified", it is meant that the modified compound is prepared by physically, enzymatically, or chemically treating the native compound to change its properties.

The emulsifier is preferably comprised in an amount ranging from 0.1 to 5.0% by weight of the microcapsule slurry, preferably between 0.5 and 2 wt % of the microcapsule slurry.

Depending on the nature of the emulsifier used, the dispersing phase may contain a minimum amount of water necessary to dissolve the emulsifier.

The microcapsules according to the present invention have a shell that is formed by interfacial polymerization. A skilled person in the art is well aware of various ways to induce interfacial polymerization.

According to an embodiment, the dispersing phase comprises nucleophiles groups, preferably with active hydrogen atoms.

According to a particular embodiment, the dispersing phase comprises a reactant, preferably chosen in the group consisting of a polyamine, a polyol, a polythiol, polyamino alcohol and mixtures thereof.

According to a particular embodiment, the reactant is a polyamine, preferably chosen in the group consisting of guanidine salts, tris-(2-aminoethyl)amine, N,N,N',N'-tetrakis(3-aminopropyl)-1,4-butanediamine, guanazole, aminoacids such as lysine, aminoalcohol such as 2-amino-1,3-propanediol, ethanolamine and mixtures thereof.

As already mentioned, the nature of the shell depends on the nature of the monomer present in the oil phase and the reactant present in the dispersing phase.

Thus, according to an embodiment, microcapsules according to the present invention are polyurea-based capsules. According to this particular embodiment, interfacial polymerization is induced by addition of a polyamine reactant in the dispersing phase to form a polyurea wall with a polyisocyanate present in the oil phase. According to another embodiment, polyurea-based capsules are formed in absence of added polyamine reactant, and result only from the autopolymerization of the at least one polyisocyanate.

According to another embodiment, microcapsules according to the present invention are polyurethane-based capsules. According to this particular embodiment, interfacial polymerization is induced by the presence of a polyol in the dispersing phase (that can be the solvent itself, for example glycerol) and/or by the addition of a polyol reactant in the dispersant phase to form a polyurethane wall with a polyisocyanate present in the oil phase. Preferably the polyol reactant is selected from the group consisting of monomeric and polymeric polyols with multiple hydroxyl groups available for reaction and mixtures thereof.

According to another embodiment, capsules according to the present invention are polyurea/polyurethane based. In that case interfacial polymerization is induced by addition of a mixture of the reactant mentioned under both precedent embodiments. Additionally, crosslinkers with both amino groups and hydroxyl groups can be used to generate polyurea/polyurethane materials. Furthermore, polyisocyanates with both urea and urethane functionalities can be used to generate polyurea/polyurethane materials.

According to another embodiment, the monomer present in the oil phase is poly maleic anhydride or poly acyl chloride and interfacial polymerization is induced by addition of a polyamine reactant or a polyol reactant (that can be the solvent present in the dispersing phase) leading respectively to polyamide-based microcapsules or polyester-based microcapsules.

According to another embodiment, the monomer present in the oil phase is polyepoxide and interfacial polymerization is induced by addition of a polyamine reactant leading to polyamino-alcohol-based microcapsules.

According to another embodiment, the monomer present in the oil phase is polyurea-polyalkoxysilane copolymer, and interfacial polymerization is induced by the hydrolysis and condensation of the alkoxysilane groups.

According to a particular embodiment, the dispersing phase comprises an aminoresin.

According to an embodiment, the mean droplet size in the two-phases dispersion is comprised between 1 and 3000 μm leading to microcapsules having a size comprised between 1 and 3000 μm.

According to a preferred embodiment, the mean droplet size is comprised between 1 and 500 μm, preferably between 5 and 50 μm.

The size of the microcapsules can be easily adjusted by the skilled person as a function of the nature of the desired application.

Optional Coating

According to a particular embodiment of the invention, at the end of step iv) one may also add to the invention's slurry a polymer selected from the group consisting of a non-ionic polysaccharide, a cationic polymer and mixtures thereof to form an outer coating to the microcapsule. Such coating will help to drive capsule deposition and retention on substrate when applied from rinse-off products so that a significant part of the capsules which have not been broken in the wash phase/upon lathering would transfer to the substrate (skin, hair fabrics) and be available for perfume release when the capsules are broken upon rubbing after drying.

Non-ionic polysaccharide polymers are well known to a person skilled in the art. Preferred non-ionic polysaccharides are selected from the group consisting of locust bean gum, xyloglucan, guar gum, hydroxypropyl guar, hydroxypropyl cellulose and hydroxypropyl methyl cellulose.

Cationic polymers are also well known to a person skilled in the art. Preferred cationic polymers have cationic charge densities of at least 0.5 meq/g, more preferably at least about 1.5 meq/g, but also preferably less than about 7 meq/g, more preferably less than about 6.2 meq/g. The cationic charge density of the cationic polymers may be determined by the Kjeldahl method as described in the US Pharmacopoeia under chemical tests for Nitrogen determination. The preferred cationic polymers are chosen from those that contain units comprising primary, secondary, tertiary and/or quaternary amine groups that can either form part of the main polymer chain or can be borne by a side substituent directly connected thereto. The weight average (Mw) molecular weight of the cationic polymer is preferably between 10,000 and 3.5M Dalton, more preferably between 50,000 and 2M Dalton.

According to a particular embodiment, one will use cationic polymers based on acrylamide, methacrylamide, N-vinylpyrrolidone, quaternized N,N-dimethylaminomethacrylate, diallyldimethylammonium chloride, quaternized vinylimidazole (3-methyl-1-vinyl-1H-imidazol-3-ium chloride), vinylpyrrolidone, acrylamidopropyltrimonium chloride, *cassia* hydroxypropyltrimonium chloride, guar hydroxypropyltrimonium chloride or polygalactomannan 2-hydroxypropyltrimethylammonium chloride ether, starch hydroxypropyltrimonium chloride and cellulose hydroxypropyltrimonium chloride. Preferably copolymers shall be selected from the group consisting of polyquaternium-5, polyquaternium-6, polyquaternium-7, polyquaternium10, polyquaternium-11, polyquaternium-16, polyquaternium-22, polyquaternium-28, polyquaternium-43, polyquaternium-44, polyquaternium-46, cassia hydroxypropyltrimonium chloride, guar hydroxypropyltrimonium chloride or polygalactomannan 2-hydroxypropyltrimethylammonium chloride ether, starch hydroxypropyltrimonium chloride and cellulose hydroxypropyltrimonium chloride As specific examples of commercially available products, one may cite Salcare® SC60 (cationic copolymer of acrylamidopropyltrimonium chloride and acrylamide, origin: BASF) or Luviquat®, such as the PQ 11N, FC 550 or Style (polyquaternium-11 to 68 or quaternized copolymers of vinylpyrrolidone origin: BASF), or also the Jaguar® (C135 or C17, origin Solvay).

According to any one of the above embodiments of the invention, there is added an amount of polymer described above comprised between about 0% and 5% w/w, or even between about 0.1% and 2% w/w, percentage being expressed on a w/w basis relative to the total weight of the slurry as obtained after step iv). It is clearly understood by a person skilled in the art that only part of said added polymers will be incorporated into/deposited on the microcapsule shell.

Microcapsule Slurry

A microcapsule slurry obtainable by the process for preparing a core-shell microcapsule slurry as defined above is also an object of the present invention.

Another object is a slurry comprising core-shell microcapsules comprising core-shell microcapsules having an oil-based core, wherein the slurry comprises below or equal to 10%, preferably below or equal to 5%, more preferably below or equal to 3% by weight of water based on the total weight of the slurry.

According to a particular embodiment, the slurry is free of water.

All the different embodiments described for the process apply for the microcapsule slurry.

Perfuming Composition

Another object of the invention is a perfuming composition comprising
(i) a microcapsules slurry as defined above, wherein the oil-based core comprises a perfume;
(ii) at least one ingredient selected from the group consisting of a perfumery carrier and a perfuming co-ingredient; and
(iii) optionally a perfumery adjuvant.

As liquid perfumery carrier one may cite, as non-limiting examples, an emulsifying system, i.e. a solvent and a surfactant system, or a solvent commonly used in perfumery. A detailed description of the nature and type of solvents commonly used in perfumery cannot be exhaustive. However, one can cite as non-limiting examples solvents such as dipropyleneglycol, diethyl phthalate, isopropyl myristate, benzyl benzoate, 2-(2-ethoxyethoxy)-1-ethanol or ethyl citrate, which are the most commonly used. For the compositions which comprise both a perfumery carrier and a perfumery co-ingredient, other suitable perfumery carriers than those previously specified, can be also ethanol, water/ethanol mixtures, limonene or other terpenes, isoparaffins such as those known under the trademark Isopar® (origin: Exxon Chemical) or glycol ethers and glycol ether esters such as those known under the trademark Dowanol® (origin: Dow Chemical Company). By "perfumery co-ingredient" it is meant here a compound, which is used in a perfuming preparation or a composition to impart a hedonic effect and which is not a microcapsule as defined above. In other words such a co-ingredient, to be considered as being a perfuming one, must be recognized by a person skilled in the art as being able to impart or modify in a positive or pleasant way the odor of a composition, and not just as having an odor.

The nature and type of the perfuming co-ingredients present in the perfuming composition do not warrant a more detailed description here, which in any case would not be exhaustive, the skilled person being able to select them on the basis of his general knowledge and according to the intended use or application and the desired organoleptic effect. In general terms, these perfuming co-ingredients belong to chemical classes as varied as alcohols, lactones, aldehydes, ketones, esters, ethers, acetates, nitriles, terpenoids, nitrogenous or sulphurous heterocyclic compounds and essential oils, and said perfuming co-ingredients can be of natural or synthetic origin. Many of these co-ingredients are in any case listed in reference texts such as the book by S. Arctander, Perfume and Flavor Chemicals, 1969, Montclair, N.J., USA, or its more recent versions, or in other works of a similar nature, as well as in the abundant patent literature in the field of perfumery. It is also understood that said co-ingredients may also be compounds known to release in a controlled manner various types of perfuming compounds.

By "perfumery adjuvant" we mean here an ingredient capable of imparting additional added benefit such as a color, a particular light resistance, chemical stability, etc. A detailed description of the nature and type of adjuvant commonly used in perfuming bases cannot be exhaustive, but it has to be mentioned that said ingredients are well known to a person skilled in the art.

Preferably, the perfuming composition according to the invention comprises between 0.05 to 30%, preferably between 0.1 and 30% by weight of microcapsules as defined above.

Consumer Product

The invention's microcapsules can advantageously be used in many application fields and used in consumer products. Microcapsules can be used in liquid form applicable to liquid consumer products or applicable to solid consumer products.

A consumer product, preferably in the form of a laundry care product, a home care product, a body care product, a skin care product, a hair care product, an air care product, or a hygiene product, comprising microcapsules as defined above, or a perfuming composition as defined above is also an object of the present invention.

Another object of the present invention is a liquid consumer product comprising:
a) from 2 to 65% by weight, relative to the total weight of the consumer product, of at least one surfactant;
b) water or a water-miscible hydrophilic organic solvent; and
c) microcapsule slurry as defined above,
d) optionally non-encapsulated perfume.

In particular a liquid consumer product, comprising:
a) from 2 to 65% by weight, relative to the total weight of the consumer product, of at least one surfactant;
b) water or a water-miscible hydrophilic organic solvent; and
c) a perfuming composition as defined above is another object of the invention.

Also a powder consumer product comprising
a) from 2 to 65% by weight, relative to the total weight of the consumer product, of at least one surfactant; and
b) a perfuming composition or microcapsules as defined above.

According to a particular embodiment, the consumer product is anhydrous.

Indeed, the microcapsules slurry obtained by the process of the invention does not need to be dried before being incorporated in anhydrous consumer product. Furthermore, the dispersing phase is compatible with anhydrous consumer product bases.

By "anhydrous", it should be understood that the liquid consumer product comprises less than about 10%, preferably less than about 5%, even preferably less than about 1%, even preferably less than about 0.5% by weight of water based on the total weight of the consumer product. According to an embodiment, the anhydrous consumer product is free of water.

In the case of microcapsules including a perfume oil-based core, the products of the invention, can in particular be of used in perfumed consumer products such as product belonging to fine fragrance or "functional" perfumery. Functional perfumery includes in particular personal-care products including hair-care, body cleansing, skin care, hygiene-care as well as home-care products including laundry care and air care. Consequently, another object of the present invention consists of a perfumed consumer product comprising as a perfuming ingredient, the microcapsules defined above or a perfuming composition as defined above. The perfume element of said consumer product can be a combination of perfume microcapsules as defined above and free or non-encapsulated perfume, as well as other types of perfume microcapsule than those here-disclosed.

The invention's microcapsules can therefore be added as such or as part of an invention's perfuming composition in a perfumed consumer product.

For the sake of clarity, it has to be mentioned that, by "perfumed consumer product" it is meant a consumer product which is expected to deliver among different benefits a perfuming effect to the surface to which it is applied (e.g. skin, hair, textile, paper, or home surface) or in the air (air-freshener, deodorizer etc). In other words, a perfumed consumer product according to the invention is a manufactured product which comprises a functional formulation also referred to as "base", together with benefit agents, among which an effective amount of microcapsules according to the invention.

The nature and type of the other constituents of the perfumed consumer product do not warrant a more detailed description here, which in any case would not be exhaustive, the skilled person being able to select them on the basis of his general knowledge and according to the nature and the desired effect of said product. Base formulations of consumer products in which the microcapsules of the invention can be incorporated can be found in the abundant literature relative to such products. These formulations do not warrant a detailed description here which would in any case not be exhaustive. The person skilled in the art of formulating such consumer products is perfectly able to select the suitable components on the basis of his general knowledge and of the available literature.

Non-limiting examples of suitable perfumery consumer product can be a perfume, such as a fine perfume, a cologne or an after-shave lotion; a fabric care product, such as a liquid or solid detergent, tablets and pods, a fabric softener, a dryer sheet, a fabric refresher, an ironing water, or a bleach; a body-care product, such as a hair care product (e.g. a shampoo, hair conditioner, a colouring preparation or a hair spray), a cosmetic preparation (e.g. a vanishing cream, body lotion or a deodorant or antiperspirant), or a skin-care product (e.g. a perfumed soap, shower or bath mousse, body wash, oil or gel, bath salts, or a hygiene product); an air care product, such as an air freshener or a "ready to use" powdered air freshener; or a home care product, such all-purpose cleaners, liquid or tablet dishwashing products, toilet cleaners or products for cleaning various surfaces, for example sprays & wipes intended for the treatment/refreshment of textiles or hard surfaces (floors, tiles, stone-floors etc.), a hygiene product such as sanitary napkins, diapers, toilet paper.

According to a particular embodiment, the consumer product is selected from the group consisting of a shampoo, a shower gel, a rinse-off conditioner, a soap bar, or a liquid detergent, a fabric softener and a floor cleaner.

According to a preferred embodiment, the consumer product is a shampoo or a rinse-off conditioner. According to another preferred embodiment, the product is a perfumed soap. According to another preferred embodiment, the product is a body wash. According to another preferred embodiment, the product is a fabric care product.

In powder detergent, it is known that bringing any additional free water to the formulation is negatively impacting the visual appearance of the powder and clearly makes the overall product look sticky. By using the microcapsules obtained by the process of the invention, it is now possible to increase further the slurry inclusion level in a powder detergent without having any drawbacks.

Another object of the invention is a powder detergent comprising:
  a powder detergent active base, and
  microcapsules prepared by the process of the invention.

Powder detergent active base in which the microcapsules of the invention can be incorporated can be found in the abundant literature relative to such products. These formulations do not warrant a detailed description here which would in any case not be exhaustive. The person skilled in the art of formulating such consumer products is perfectly able to select the suitable components on the basis of his general knowledge and of the available literature.

Among the liquid detergent consumer product, there are the individual liquid detergent pods having almost an anhydrous composition. The inclusion level of standard microcapsules in this very specific format is limited due the presence of water in the slurry as it can easily dissolve the film (typically PvOH).

The use of microcapsules obtained by the process of the invention increases the amount of capsules within the formulation without compromising the film properties.

Another object of the invention is a liquid detergent pod comprising:
  a liquid detergent active base, and
  microcapsules prepared by the process of the invention,
    wherein the liquid detergent active base and the microcapsules slurry are embedded in a pod having at least one compartment.

The pod generally consists of a film made of PVOH.

Liquid detergent active base in which the microcapsules of the invention can be incorporated can be found in the abundant literature relative to such products. These formulations do not warrant a detailed description here which would in any case not be exhaustive. The person skilled in the art of formulating such consumer products is perfectly able to select the suitable components on the basis of his general knowledge and of the available literature.

Finally a last object of the invention is a solid scent booster composition comprising:
  a carrier, and
  microcapsules prepared by the process of the invention.

According to an embodiment, the solid scent booster composition is in a pastillized form.

Typically, the microcapsules slurry is mixed with the carrier in a molten state to obtain a homogeneous mixture. Then, the mixture can be poured drop wise on a support to obtain solidified pastilles.

Any material that can be easily molten and solidified can be used a carrier in the present invention.

According to an embodiment, the carrier is chosen in the group consisting of PEG, fatty alcohols and mixtures thereof.

PEG has preferably a molecular weight greater than 1000 g/mol, preferably between 1000 and 8000 g/mol. Fatty alcohols have preferably 20 or more carbon atoms.

Preferably, the consumer products as defined above comprises from 0.05 wt %, preferably from 0.1 to 15 wt %, more preferably between 0.2 and 5 wt %, even more preferably between 1 and 5% of the microcapsules of the present invention, these percentages being defined by weight relative to the total weight of the consumer product. Of course the above concentrations may be adapted according to the olfactive effect desired in each product.

The invention will now be further described by way of examples. It will be appreciated that the invention as claimed is not intended to be limited in any way by these examples.

EXAMPLES

Example 1

Preparation of Polyurethane Microcapsules According to the Invention 60 g of glycerol (Origin: Alfa Aesar) containing 3% (w/w) of casein sodium salt (Origin: Sigma Aldrich) were introduced into a reactor and heated to 70° C. The oil phase containing 30 g of perfume A (see table 1) and 0.6 g of a polyisocyanate (trimethylol propane adduct of xylylene diisocyanate, Takenate® D-110N, origin: Mitsui Chemicals) was added in the glycerol phase then mechanically stirred at 800® during 5 min to obtain an emulsion. The emulsion was kept at 300 RPM for 7 hours at 70° C. Then, the stirring was stopped and the system was cooled down at room temperature. The average size for this microcapsules suspension was close to 15 µm.

TABLE 1

| Composition of perfume A | |
|---|---|
| Ingredients | % in oil |
| Ethyl 2-methyl-pentanoate | 0.25 |
| (Z)-3-hexen-1-ol acetate | 0.30 |
| 2,4-Dimethyl-3-cyclohexene-1-carbaldehyde | 1.25 |
| Rose oxide | 0.40 |
| Hexyle Isobutyrate | 3.80 |
| Menthone | 0.50 |
| Menthol | 3.20 |
| linallyle acetate | 10.20 |
| carbinol BDM acetate | 2.05 |
| terpenyle acetate | 9.50 |
| citronellyle acetate | 7.30 |
| verdyle acetate | 3.00 |
| nopyle acetate | 7.60 |
| betaionone | 0.50 |
| verdyle Propionate | 4.20 |
| Hedione ®[1) | 11.00 |
| Ald hexylcinnamique | 13.50 |
| Tinogard ®DA | 0.50 |
| Tinogard ® TT DD | 0.20 |
| Butylated hydroxytoluene | 0.10 |
| 1-(5,5-dimethyl-1-cyclohexen-1-yl)-4-penten-1-one | 0.10 |
| (1'R)-2-[2-(4'-METHYL-3'-CYCLOHEXEN-1'-YL)PROPYL]CYCLOPENTANONE | 9.40 |
| MIP Isopropyl Myristate | 11.15 |

[1)Methyl dihydrojasmonate, Origin: Firmenich SA, Geneva, Switzerland

Example 2

Preparation of poly(urea-urethane) Microcapsules According to the Invention 60 g of glycerol phase containing 3% (w/w) of casein sodium salt (Origin: Sigma Aldrich) were introduced in a reactor and heated to 70° C. The oil phase, prepared by mixing 0.6 g of a polyisocyanate (trimethylol propane adduct of xylylene diisocyanate, Takenate® D-110N, origin: Mitsui Chemicals) and 30 g of perfume A (see table 1), was added in the glycerol phase. The emulsion was obtained by using an anchor rotor at 800 RPM during 5 minutes and kept at 70° C. 0.23 g of guanidine carbonate (Origin: Alfa Aesar) were dissolved in 8.8 g of glycerol and added to the emulsion. The emulsion was kept at 300 RPM for 7 hours at 70° C. The stirring was then stopped and the system was cooled down at room temperature. The average size of the resulting microcapsules was close to 15 µm.

Example 3

Perfume Retention from Microcapsules According to the Invention

Figure 1:
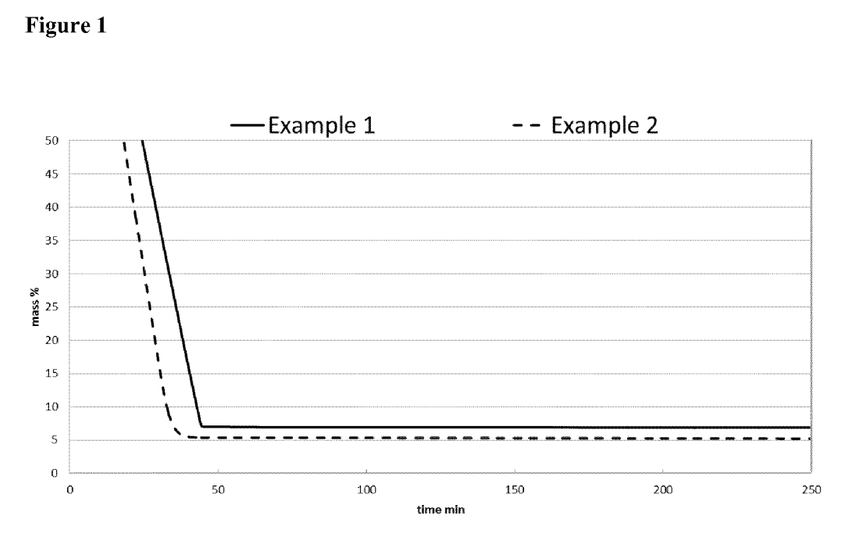
FIG. 1 represents TGA curves of microcapsules prepared according to the process of the invention.

Microcapsules prepared in examples 1 and 2 were washed 3 times with water to remove glycerol and analyzed with Thermogravimetric analyzer (TGA, Mettler-Toledo, Switzerland) to assess their perfume retention. The microcapsules sample (10 to 20 mg) was introduced into an aluminium oxide crucible and its remaining mass was determined by TGA under controlled temperature and a constant flow of nitrogen of 20 mL/min. The sample was heated from 25° C. to 50° C. at a rate of 10° C./min then the temperature was kept constant for about two hours. Results are shown in FIG. 1. In both cases, the isotherm curves present a plateau which indicates good perfume retention.

Example 4

Figure 2:
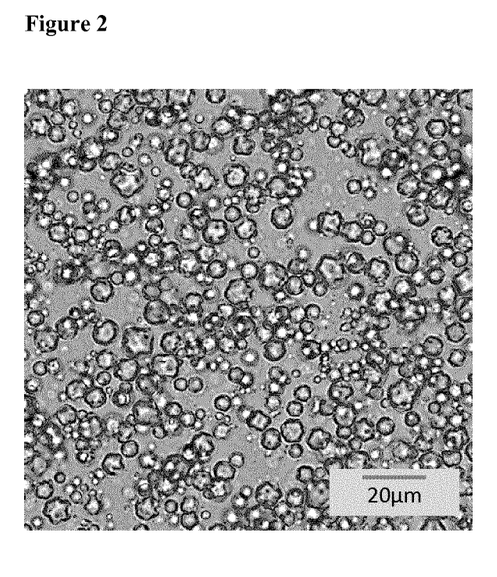
FIG. 2 and FIG. 3 represent micrographs of microcapsules prepared according to the process of the invention.

Preparation of poly(urea-urethane) Microcapsules According to the Invention 60 g of glycerol phase containing 1% (w/w) of polyvinylpyrrolidone (Origin: sigma Aldrich) and 1% (w/w) of poly(l-vinylpyrrolidone co-vinyl acetate) (Origin: Sigma Aldrich) were introduced in a reactor and heated to 50° C. The oil phase prepared by dissolving at 50° C. 2 g of a polyisocyanate (trimethylol propane adduct of xylylene diisocyanate, Takenate® D-110N, origin: Mitsui Chemicals) and 30 g of perfume A (see table 1) was added to the glycerol phase. The emulsion was obtained by stirring this mixture with an anchor rotor at 600 RPM during 3 minutes at 50° C. 0.28 g of 1,2-diaminocyclohexane (Origin: Sigma Aldrich) mixed with 7.7 g of glycerol were added to the emulsion that was then kept at 300 RPM for 5 hours at 50° C. At the end of the polymerization process, the stirring was stopped and the system was cooled down at room temperature. The average size of the resulting microcapsules was closed to 10 µm (see FIGS. 2a and 2b).

Example 5

Preparation of Poly(Amino-Alcohol) Microcapsules According to the Invention Capsules A5:

60 g of glycerol phase containing 3% (w/w) of casein sodium were introduced into a reactor and heated to 70° C. The oil phase was prepared by dissolving 0.6 g poly[(o-cresyl glycidyl ether)-co-formaldehyde] (Origin: sigma Aldrich) in 30 g of perfume A (see table 1), was added in the glycerol phase. The emulsification was obtained by shearing with the anchor rotor at 600 RPM during 3 min at 70° C. 0.2 g of tris-2-aminoethylamine (Origin: Sigma Aldrich) mixed with 9.1 g of glycerol were added to the emulsion, which was then kept under stirring at 300 RPM for 6 hours at 70° and overnight at 80° C. The stirring was stopped and the system was cooled down at room temperature. The average size of the resulting microcapsules was closed to 10 µm.

Capsules B5:

Solution (60 g) of casein sodium (3 wt %) in glycerol was placed into a reactor. The oil phase, composed of trimethylol triglycidyl ether (2.02 g, Sigma Aldrich) and perfume B (30 g), was added dropwise at room temperature to the glycerol phase. The resulting mixture was stirred at 600 RPM with an anchor rotor during 2 minutes at 50° C. to obtain an emulsion. Then a solution of 1,2-diaminocyclohexane (1.14 g, Sigma Aldrich) in glycerol (5 g) was added over the course of one hour. The reaction mixture was kept under stirring at 300 rpm during one hour at 50° C. and then four hours at 80° C.

TABLE 2

Composition of Perfume B

| Raw mat | % in oil |
|---|---|
| Ethyl 2-methyl-pentanoate | 3.20% |
| Eucalyptol | 7.80% |
| 2,4-Dimethyl-3-cyclohexene-1-carbaldehyde [1] | 0.75% |
| Aldehyde C10 | 0.75% |
| Citronellyl Nitrile | 4.30% |
| Isobornyl acetate | 3.00% |
| Verdox ®[2] | 9.80% |
| Citronellyl Acetate | 1.30% |
| 2-Methylundecanal | 3.00% |
| Diphenyloxide | 0.80% |
| Aldehyde C12 | 1.30% |
| Dicyclopentadiene acetate | 9.85% |
| Ionone beta | 3.30% |
| Undecalactone gamma | 18.75% |
| Hexyl Salicylate | 15.90% |
| Benzyl Salicylate | 16.20% |
| TOTAL | 100% |

[1] Origin: Firmenich SA, Geneva, Switzerland
[2] Trademark from IFF; 2-tert-butyl-1-cyclohexyl acetate Capsules C5:

Solution (60 g) of casein (3 wt %) in glycerol was placed into a reactor. The oil phase, composed of poly[(o-cresyl glycidyl ether)-co-formaldehyde] (1.20 g, Sigma Aldrich) and perfume B (30 g), was added dropwise at room temperature to the glycerol phase. The resulting mixture was stirred at 600 rpm with an anchor rotor during 2 minutes at 50° C. to obtain an emulsion. Then a solution of tris-2-aminoethylamine (2.70 g, Sigma Aldrich) in glycerol (2 g) was added over the course of one hour. The reaction mixture was kept under stirring at 600 rpm during one hour at 50° C. A solution of DABCO (0.05 g) in glycerol (2.5 g) was added and the reaction mixture was warmed at 80° C. for two hours.

Capsules D5:

Solution (60 g) of casein (3 wt %) in glycerol was placed into a reactor. The oil phase, composed of poly[(o-cresyl glycidyl ether)-co-formaldehyde] (1.20 g, Sigma Aldrich) and perfume B (30 g), was added dropwise at room temperature to the glycerol phase. The resulting mixture was stirred at 600 rpm with an anchor rotor during 2 minutes at 50° C. to obtain an emulsion. Then a solution of 2-ethanolamine (2.70 g, Sigma Aldrich) in glycerol (2 g) was added over the course of one hour. The reaction mixture was kept under stirring at 600 rpm during one hour at 50° C. A solution of DABCO (0.05 g) in glycerol (2.5 g) was added and the reaction mixture was warmed at 80° C. for two hours.

Example 6

Preparation of Poly(Urea-Alkylsiloxane) Microcapsules According to the Invention Preparation of the oil phase: Two amine solution, prepared by mixing 0.23 g of 1,2-diaminocyclohexane diluted in 1 g of Neobee (Origin: Stepan) and 0.037 g of 1,2-diaminopropane (Origin: Sigma Aldrich) diluted in 1 g Neobee at room temperature, were successively added to a 1.26 of 3-(triethoxysilyl)propyl isocyanate (Origin: Sigma Aldrich) dissolved at 60° C. in 10 g of perfume C (see table 3). The reaction mixture was kept at 60° C. for 1 hour.

Figure 3:
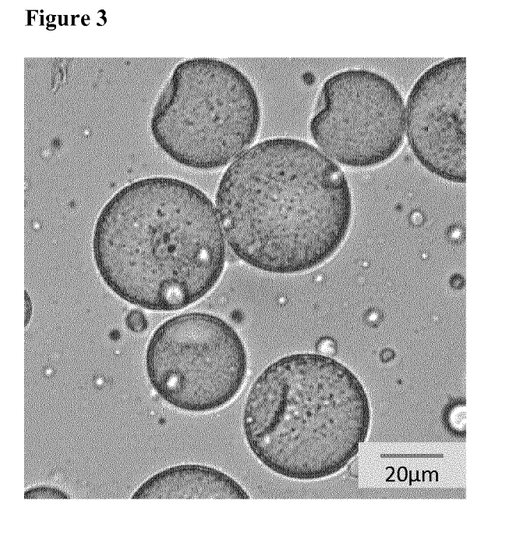

60 g of glycerol contain 1% (w/w) of Superstab Gum Arabic (from Nexira), 1% (w/w) of acid lignosulfonic sodium salt (Sigma Aldrich) and 5% (w/w) of di-ionized water were placed in a reactor and maintained at 50° C. The oil phase was heated to 50° C. and added in the glycerol phase. The emulsification was achieved by stirring with an anchor rotor at 600 RPM during 3 minutes at 50° C. The emulsion's temperature was increased to 75° C. and 10 g of 10% HCl solution were added during one hour. The emulsion was kept under mechanical agitation for 5 hours at 75° C. Then 10 g of 10% ammonia solution were added during one hour and the system was let at 75° C. for 16 h. At the end of the microencapsulation process, the stirring was stopped and the system was cooled down at room temperature. The resulting microcapsules are shown in FIG. 3. The average size of the microcapsules was close to 15 µm.

TABLE 3

Composition of perfume C

| Raw Material | % in oil |
|---|---|
| Ethyl 2-methyl-pentanoate | 4.00 |
| 2,4-Dimethyl-3-cyclohexene-1-carbaldehyde | 4.00 |
| Allyl Heptanoate | 6.60 |
| (Z)-3-hexen-1-ol Butyrate | 1.30 |
| Allyl amyl glycolate | 13.10 |
| Delta Damascone | 2.00 |
| Verdyl acetate | 24.30 |
| Methylnaphtylcetone | 1.30 |
| Hedione ®[1] | 6.60 |
| Iso E Super ® [2] | 19.70 |
| Ald. Hexylcinnamique | 13.10 |
| Habanolide ® [3] | 4.00 |
| Total | 100 |

[1] Methyl dihydrojasmonate, Origin: Firmenich SA, Geneva, Switzerland
[2] 1-(octahydro-2,3,8,8-tetramethyl-2-naphtalenyl)-1-ethanone, Origin: IFF, USA
[3] pentadecenolide, Origin: Firmenich SA, Geneva, Switzerland

Example 7

Preparation of Polyamide Microcapsules According to the Invention

Preparation of the Continuous Phase:

3 g of Superstab Gum Arabic (Nexira), were dissolved at room temperature in 97 g of glycerol containing 10% (w/w) of di-ionized water and placed into a reactor. The oil phase, composed of 2.03 g of terephtaloyl chloride (Sigma Aldrich) and 30 g of perfume D, was added dropwise at room temperature to the glycerol phase. The resulting mixture was stirred at 600 RPM with an anchor rotor during 3 minutes to obtain an emulsion. Then 5.85 g of tris-2-aminoethylamine (Sigma Aldrich) were added during one hour. The reaction mixture was kept during 4 hours under stirring at 300 RPM at room temperature. Microcapsules were obtained with an average size of 40 μm Perfume D was prepared by admixing at equal mass 5 perfumery ingredients: Hexyl salicylate, Romascone®[1], Cyclosal[2], Vertenex®[3], and Verdox®[4].

[1] (methyl 2,2-dimethyl-6-methylene-1-cyclohexanecarboxylate, origin: Firmenich SA, Geneva, Switzerland);
[2] ((+−)-3-(4-isopropylphenyl)-2-methylpropanal, origin: Firmenich SA, Geneva, Switzerland);
[3] (4-tert-butyl-1-cyclohexyl acetate, origin: International Flavors and Fragrances, USA);
[4] (2-tert-butyl-1-cyclohexyl acetate, origin: International Flavors and Fragrances, USA).

Example 8

Preparation of Poly(Urea-Urethane) Microcapsules According to the Invention 60 g of glycerol solution containing 1% (w/w) of polyvinylalcohol Mowiol 18-88 (Sigma Aldrich) and 5% (w/w) of di-ionized water were placed into a reactor and heated to 50° C. The oil phase, prepared by dissolving at room temperature 2 g of a polyisocyanate (trimethylol propane adduct of xylylene diisocyanate, Takenate® D-110N, origin: Mitsui Chemicals), 30 g of perfume D, was added to the glycerol phase. The resulting mixture was stirred at 600 RPM for 3 min to obtain an emulsion. The stirring rate was decreased to 300 RPM while the temperature of the emulsion was increased to 70° C. 0.23 g of Guanidine Carbonate, dissolved in 7.85 g of glycerol, was added into the reactor and the reaction mixture was kept under stirring for 7 hours at 70° C. The average size of the obtained microcapsules was close to 15 μm.

Example 9

Preparation of Polyester Microcapsules According to the Invention

Capsule A9

95 g of a solution of Superstab Gum Arabic (3 g, Nexira) in 97 g of glycerol, containing 10% (w/w) of di-ionized water, was placed into a reactor in the presence of trimethylolpropane (2.7 g, Sigma-Aldrich). The oil phase, composed of 1,3,5-benzene tricarbonyl chloride (1.77 g, Sigma Aldrich) and perfume B (25 g), was added dropwise at room temperature to the glycerol phase. The resulting mixture was stirred at 600 rpm with an anchor rotor during 3 minutes at room temperature to obtain an emulsion. Then a solution of triethanolamine (2.98 g, Sigma Aldrich) in glycerol (5 g) was added dropwise. The reaction mixture was kept under stirring at 600 rpm during two hours at 30° C. and then at 120° C. for two hours under gentle stirring.

Capsule B9

In a 150 mL beaker, introduce glycerol solutions of PVP (22.36 g, 1 wt %, origin: BASF) and PVP-co-PVAc (22.36 g, 1 wt %, origin: BASF). Triethanolamine (0.95 g, origin: Aldrich) and triethylamine (1.29 g, origin: Aldrich) were added in the glycerol phase. Reaction mixture was stirred with a mechanical stirrer at RT.

In a 50 mL flask, terephtaloyl chloride (1.29 g, origin: Aldrich) and perfume D (19.93 g, origin: Firmenich SA) were mixed under magnetic stirring for 15 min to afford an oil phase. The oil phase was added dropwise to the glycerol phase under vigorous mechanical stirring to afford an emulsion. The reaction mixture was stirred at RT until the formation of microcapsules.

Example 10

Stability Performance in a Shower Gel Base

Stability performance in a shower gel composition (see table 4) of microcapsules obtained by the process of the invention was assessed.

TABLE 4

| Shower gel base composition | |
| --- | --- |
| Ingredients | Quantity (%) |
| Water | 49.350 |
| Tetrasodium EDTA [1] | 0.050 |
| Acrylates Copolymer [2] | 6.0 |
| Sodium C12-C15 Pareth Sulfate [3] | 35.0 |
| Sodium hydroxide [4] | 1.0 |
| Cocamidopropyl Betaine [5] | 8.0 |
| Methylchloroisothiazolinone (and) Methylisothiazolinone [6] | 0.1 |
| Citric Acid (40%) | 0.5 |

[1] EDETA B POWDER (BASF)
[2] CARBOPOL AQUA SF-1 POLYMER (NOVEON)
[3] ZETESOL AO 328 U (ZSCHIMMER & SCHWARZ)
[4] SODIUM HYDROXIDE 20% aqueous solution
[5] TEGO-BETAIN F 50 (GOLDSCHMIDT)
[6] KATHON CG (ROHM & HAAS)

Figure 4:
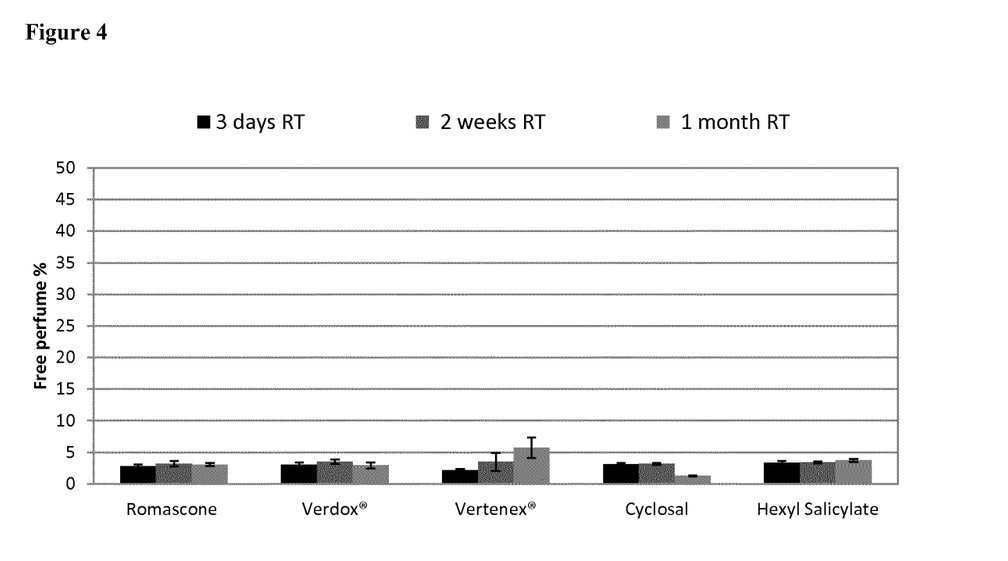
FIG. 4 represents stability results (perfume leakage) of microcapsules prepared by the process of the invention in a shower gel base.

Microcapsules prepared in example 8 were introduced in a shower gel base (see table 4) in such way to obtained 0.5% of perfume content. The sample was kept at room temperature and the stability of the microcapsules was assessed at different time by quantifying the free perfume in the base. The result depicted in FIG. 4 shows good storage stability of the microcapsules in shower gel base.

Example 11

Fabric Softener Base Formulation Comprising Microcapsules Prepared by the Process of the Invention Microcapsule D5 prepared in example 5 (0.19 g) are introduced in a fabric softener base (49.8 g, see table 5) in such way to obtained 0.11% of perfume content.

TABLE 5

| Fabric softener base composition | |
|---|---|
| Ingredients | Quantity (%) |
| Water | 90.72 |
| Stepantex VL 90A | 8.88 |
| Calcium chloride solution at 10% | 0.36 |
| Proxel GXL | 0.04 |

Example 12

Powder Detergent Formulation Comprising Microcapsules Prepared by the Process of the Invention The microcapsules obtained in Example 8 are incorporated in a commercially available powder detergent (Persil Universal, origin: Henkel, Germany) at a inclusion level of respectively 1% and 1.5%

Powder Detergent Formulation:
sodium percarbonate, benzenesulfonic acid, C10-13-alkyl derivs sodium salts, sodium carbonate, sulfuric acid, mono C12-18 alkyl esters sodium salts, alcohols ethoxylated.

Example 13

Liquid Detergent Dose Formulation Comprising Microcapsules Prepared by the Process of the Invention Incorporation of microcapsules obtained in Example 8 are introduced at the rate of 1.5% and 3% slurry in a commercially available standard unit dose liquid detergent base with single compartment from Unilever called Persil Small & Mighty Bio Capsules, origin: Unilever, UK), packaged in PVOH sachets.

Persil Small & Mighty Bio Capsules Formulation:
mea-dodecylbenzesulfonate, mea-hydrogenated cocoate, propylene glycol, c12-15 pareth-7, aqua, glycerin, polyvinyl alcohol, parfum, pentasodium ethylenediamine tetramethylene phosphonate, ethanolamine, sorbitol, mea-sulfate, pvp, subtilisin, glycol, butylphenyl methypropional, starch, hexal cinaamal, boronic acid, (4,formylphenal), limonene, lianlool, dosodium distyrylbiphenyl disulfonate, alpha-isomethyl ionone, talc, amylase, polymeric blue colourant, sodium chloride, mannamase, polymeric yellow colourant.

The same capsules introduced at the rate of 1.5% and 3% slurry in a commercially available standard unit dose liquid detergent base with multi-compartments from P&G called Ariel Pods Capsule packaged in PVOH sachets.

Ariel Pods Capsules Formulation:
mea-dodecylbenzenesulfonate, propylene glycol, c12-14 pareth-7, mea-laureth sulfate, aqua, pei ethoxylate, glycerin, parfum, co-polymer of peg/vinyl acetate, dodecylbenzene sulfonic acid, potassium sulfite, magnesium chloride, peg/ppg-10/2 propylheptyl ether, benzyl salicylate, hydrogenated castor oil, ethanolamine, polystyrene, hexyl cinnamal, citronellol, butylphenyl methylpropional, sodium formate, sorbitol, protease, linalool, coumarin, tripropylene glycol, 2-propenoic acid, polymer with ethenylbenzene, disodium distyrylbiphenyl disulfonate, geraniol, sulfuric acid, glycosidase, sodium acetate, cellulase, colorant, sodium lauryl sulfate, sodium sulfate, sodium polynaphthalenesulfonate

Example 14

Polyethyleneglycol Based Solid Scent Booster Comprising Microcapsules Prepared by the Process of the Invention 29.1 g Polyethyleneglycol (PEG) 4000 are heated to obtain a water clear liquid. 0.9 g of microcapsule slurry prepared in example 8 are added to the molten PEG and the mixture is shortly agitated by means of a magnetic stir bar to obtain a homogenous mixture. The liquid capsule dispersion is then poured drop wise (to obtain pastilles) or in a slow, continuous and strand like manner onto a stainless steel plate. After solidification the PEG pastilles are collected. In the case of strands the PEG material is broken into small pieces and finally also applied as solid scent booster in wash applications.

The invention claimed is:

1. A process for preparing a microcapsule slurry, said process comprising the steps of:
   (i) dissolving a monomer in an oil phase comprising a hydrophobic active ingredient;
   (ii) preparing a dispersing phase comprising an emulsifier, wherein the dispersing phase is not miscible with the oil phase, and wherein the dispersing phase is hydrophilic;
   (iii) adding the oil phase to the dispersing phase to form a two-phases dispersion; and
   (iv) applying conditions sufficient to induce interfacial polymerization and form core-shell microcapsules in the form of a slurry;
   wherein the monomer is susceptible to react during the interfacial polymerisation to form the microcapsules in the form of a slurry;
   said process being characterized in that a content of water in the dispersing phase is below or equal to 10% by weight based on a total weight of the dispersing phase.

2. The process according to claim 1, wherein the content of water in the dispersing phase is below or equal to 5% by weight based on the total weight of the dispersing phase.

3. The process according to claim 2, wherein the dispersing phase does not comprise water.

4. The process according to claim 1, wherein the dispersing phase comprises nucleophiles groups.

5. The process according to claim 1, wherein the dispersing phase comprises a solvent chosen from the group consisting of glycerol, 1,4-butanediol, ethylene glycol and mixtures thereof.

6. The process according to claim 1, wherein the monomer in the oil phase is chosen from the group consisting of at least one polyisocyanate, poly maleic anhydride, poly acyl chloride, polyepoxide, acrylate monomers and polyalkoxysilane.

7. The process according to claim 1, wherein the dispersing phase comprises a polyamine.

8. The process according to claim 1, wherein the dispersing phase comprises a polyol.

9. The process according to claim 1, wherein the emulsifier is chosen from the group consisting of gum Arabic, lignin sulfonate, soy protein, sodium caseinate, gelatin, bovine serum albumin, sugar beet pectin, hydrolyzed soy protein, hydrolyzed sericin, Pseudocollagen, Biopolymer SA-N, Pentacare-NA PF, co-polymers of acrylamide and acrylic acid, acrylic co-polymers bearing a sulfonate group, anionic polyvinyl alcohol, cationic polyvinyl alcohol, polyvinylpyrrolidone, polyvinyl alcohol, co-polymers of vinyl ethers and maleic anhydride, modified polyvinyl alcohol, modified starch, modified cellulose, polysaccharides and mixtures thereof.

10. A microcapsule slurry obtained by the process as defined in claim 1, wherein the slurry comprises below or equal to 10% by weight of water based on a total weight of the slurry.

11. A perfuming composition comprising:
(i) a microcapsule slurry as defined in claim 10, wherein the hydrophobic active ingredient comprises a perfume;
(ii) at least one ingredient selected from the group consisting of a perfumery carrier and a perfuming co-ingredient; and
(iii) optionally a perfumery adjuvant.

12. A liquid consumer product comprising:
a) from 2 to 65% by weight, relative to a total weight of the liquid consumer product, of at least one surfactant;
b) water or a water-miscible hydrophilic organic solvent; and
c) a microcapsule slurry as defined in claim 10.

13. A powder consumer product comprising:
a) from 2 to 65% by weight, relative to a total weight of the powder consumer product, of at least one surfactant; and
b) a microcapsule slurry as defined in claim 10.

14. The liquid consumer product according to claim 12 in the form of an anhydrous liquid consumer product.

15. The process according to claim 1, wherein the hydrophobic active ingredient comprises a perfume.

16. The process according to claim 7, wherein the dispersing phase comprises a polyamine chosen from the group consisting of guanidine salts, tris-(2-aminoethyl)amine, N,N,N',N'-tetrakis(3-aminopropyl)-1,4-butanediamine, guanazole, aminoacids, aminoalcohol, ethanolamine and mixtures thereof.

17. The microcapsule slurry according to claim 10, wherein the slurry comprises below or equal to 5% by weight of water based on the total weight of the slurry.

18. The microcapsule slurry according to claim 17, wherein the slurry comprises below or equal to 3% by weight of water based on the total weight of the slurry.

19. The liquid consumer product according to claim 12, wherein the liquid consumer product is in the form of a laundry care product, a home care product, a body care product, a skin care product, an air care product, or a hygiene product.

* * * * *